United States Patent
Darmenton et al.

(10) Patent No.: US 6,326,033 B1
(45) Date of Patent: Dec. 4, 2001

(54) COMPOSITIONS COMPRISING SANTALINS, SANTARUBINS FOR ARTIFICIALLY COLORING THE SKIN

(75) Inventors: Patrick Darmenton, Bourg la Reine; Delphine Allard, Colombes; Serge Forestier, Claye Souilly, all of (FR)

(73) Assignee: Societe L'Oreal S.A., Paris (FR)

( * ) Notice: Subject to any disclaimer, the term of this patent is extended or adjusted under 35 U.S.C. 154(b) by 0 days.

(21) Appl. No.: 09/381,657

(22) PCT Filed: Mar. 4, 1998

(86) PCT No.: PCT/FR98/00422

§ 371 Date: Dec. 8, 1999

§ 102(e) Date: Dec. 8, 1999

(87) PCT Pub. No.: WO98/44902

PCT Pub. Date: Oct. 15, 1998

(30) Foreign Application Priority Data

Apr. 4, 1997 (FR) .................................................. 97 04158

(51) Int. Cl.$^7$ ............................ A61K 35/78; A61K 7/00; A61K 7/021; A61K 7/42
(52) U.S. Cl. ............................ 424/725; 424/401; 424/59; 424/63
(58) Field of Search ................................. 424/195.1, 401, 424/59, 63, 725

(56) References Cited

U.S. PATENT DOCUMENTS 4,933,177 * 6/1990 Grollier et al. .

FOREIGN PATENT DOCUMENTS

| 0 072 298 | 2/1983 | (EP) . |
| 2 483 228 | 12/1981 | (FR) . |
| 2 543 434 | 10/1984 | (FR) . |

OTHER PUBLICATIONS

Arnone et al. J.C.S. Perkin, vol. 19, pp. 2116–2118, 1977.*
Arnone et al. Phytochemistry, vol. 20, No. 4, pp. 799–801, 1981.*
Verghese. Cosmetics and Toiletries, vol. 101, No. 4, pp. 69–71, 1986.*

* cited by examiner

Primary Examiner—Francisco Prats
Assistant Examiner—Susan D Coe
(74) Attorney, Agent, or Firm—Burns, Doane, Swecker & Mathis, L.L.P.

(57) ABSTRACT

The invention relates to cosmetic and/or dermopharmaceutical compositions comprising at least one extract of redwood as a skin-coloring agent; the compositions may further comprise dihydroxyacetone. The invention also relates to cosmetic and/or dermopharmaceutic compositions comprising at least one santalin or santarubin. The compositions are applied to color the skin with a color similar to natural tanning.

17 Claims, No Drawings

COMPOSITIONS COMPRISING SANTALINS, SANTARUBINS FOR ARTIFICIALLY COLORING THE SKIN

The present invention relates to novel cosmetic and/or dermatological compositions comprising at least one specific compound, namely a redwood extract, in order to confer on the skin an artificial colouring similar to natural tanning, and to their uses in the abovementioned cosmetics field.

In this day and age, it is important to look well and a tanned skin is always a sign of good health. However, natural tanning is not always desirable insofar as it requires prolonged exposure to UV radiation, in particular to UV-A radiation, which causes browning of the skin but, on the other hand, can induce a detrimental change in the latter, in particular in the case of sensitive skin or skin continually exposed to solar radiation. It is therefore desirable to find an alternative to natural tanning which is compatible with the requirements of such skin.

The majority of cosmetic products intended for the artificial tanning of the skin are based on carbonyl derivatives which make possible the formation of coloured products by interaction with the amino acids of the skin.

To this end, it is known that dihydroxyacetone or DHA is a particularly advantageous product which is commonly used in cosmetics as an agent for the artificial tanning of the skin; applied to the latter, in particular to the face, it makes it possible to obtain a tanning or browning effect with an appearance similar to that which can result from prolonged exposure to the sun (natural tanning) or under a UV lamp.

However, the use of DHA can exhibit certain disadvantages. Thus, DHA has an unfortunate tendency, more or less pronounced, depending on the nature of the medium in which it is formulated, to decompose over time, this decomposition generally being reflected in the long run by an undesirable yellowing of the compositions in which it is present. Such a phenomenon means that the activity of the DHA, in particular its ability to colour the skin, may be decreased at the time of the application of these compositions to the skin. Thus, the intensity of the colouring obtained on the skin may appear to be still insufficient.

Another disadvantage of DHA is the slowness with which the colouring develops: this is because several hours (3 to 5 hours in general) are required for the colouring to develop. Furthermore, the colouring produced on the skin with DHA is often regarded as too yellow by users. There therefore exists an increasing demand for self-tanning products which act rapidly and which confer a colouring closer to natural tanning.

For the purpose of responding to this need, provision has been made to combine DHA with various compounds: thus, the document WO 95/15742 discloses the combination of DHA with amino acids. However, such combinations are very seldom used insofar as their use requires either a two-step application or complex separate packagings. The document FR-2,726,761 discloses, for its part, the combination of DHA with lawsone and/or juglone: here again, this combination is not very satisfactory, due this time to the risks of sensitization which it exhibits.

Thus, a search is still being maintained for new compounds and new compositions which make it possible to artificially confer on the skin a colouring similar to natural tanning in a simple, efficient, rapid and risk-free way.

In point of fact, following much research carried out in the field of the artificial colouring of the skin, the Applicant Company has now discovered that the use of specific compounds, furthermore known in the state of the art as dyes, makes it possible to confer on the skin a lasting artificial colouring similar to natural tanning which is achieved immediately after application to the skin.

The subject-matter of the present invention is therefore a novel cosmetic and/or dermatological composition, characterized in that it comprises, in a cosmetically acceptable vehicle, at least one redwood extract as agent for colouring the skin.

Within the meaning of the present invention, the term "agent for colouring the skin" is understood to mean a compound having a specific affinity for the skin which allows it to confer on the latter a lasting artificial colouring. The term "lasting colouring" is understood to mean a colouring which is removed neither with water nor using a solvent and which withstands both rubbing and washing with a solution comprising surfactants. Such a lasting colouring is therefore distinguished from the superficial and short-lived colouring contributed, for example, by a make-up product or by face painting.

A further subject-matter of the present invention is the novel use of at least one extract as defined above in or for the manufacture of cosmetic and/or dermatological compositions intended to confer on the skin an artificial colouring similar to natural tanning.

Another subject-matter of the present invention is a process for the cosmetic treatment of the skin intended to confer on it an artificial colouring similar to natural tanning, characterized in that it consists in applying, to the skin, an effective amount of an extract or of a cosmetic composition as defined above.

The compositions and the uses in accordance with the invention make it possible to obtain an artificial colouring similar to natural tanning in an exceptionally short period of time. An immediate colouring is thus obtained which makes it possible to see the application and consequently makes possible better homogeneity in the spreading of the composition over the skin and therefore of the colouring which results therefrom. Furthermore, the artificial colouring obtained on the skin according to the invention is extremely close to natural tanning and also highly resistant to water and to time (it can persist on the skin for several days).

Other characteristics, aspects and advantages of the present invention will become apparent on reading the detailed description which will follow.

The compounds used in the present invention are redwood extracts: these redwoods include those known as "soluble" redwoods and those known as "insoluble" redwoods.

The term ""soluble" redwoods" generally encompasses different species of the genus "Cesalpinia", such as *Cesalpinia sappan*, more commonly known as sappanwood, *Cesalpinia brasiliensis*, also known as brazilwood, *Cesalpinia crista* or *Cesalpinia echinata*.

The term ""insoluble" redwoods" generally encompasses the Asian and West African species of redwoods of the genus "Pterocarpus" and of the genus "Baphia": these woods are, for example, *Pterocarpus santalinus, Pterocarpus osun, Pterocarpus soyauxii, Pterocarpus erinaceus, Pterocarpus indicus* or *Baphia nitida*. These woods may also be known as padauk, sandalwood, narrawood, camwood or barwood.

Extracts which can be used in the present invention can thus, for example, be obtained from red sandalwood (*Pterocarpus santalinus*) by basic aqueous extraction, such as the product sold under the trade name "Santal Concentré SL 709C" by the company Copiaa, or alternatively by means of solvent extraction of sandal powder, such as the product sold under the trade name "Santal Poudre SL PP" by the same company Copiaa. Mention may also be made of the aqueous/alcoholic extract of red sandalwood powder from the company Alban Müller.

Extracts which are also suitable for the present invention can be obtained from reddish wood, such as camwood (*Baphia nitida*) or barwood (*Pterocarpus soyauxii, Pterocarpus erinaceus*): the latter is thus split up and then milled: a conventional alcoholic extraction or an extraction by percolation is subsequently carried out on this milled material in order to collect a pulverulent extract particularly suited to the implementation of the present invention.

These extracts are preferably obtained from the corresponding red heartwood.

Extracts from redwoods known as "insoluble" redwoods will preferably be employed in the present invention.

Compounds extracted from such woods and which are particularly well suited to the implementation of the present invention are, for example, santalins A, B and C and santarubins A, B and C.

Some of these compounds are known as dyes for foodstuffs or as dyes for leather or for wool. They are described, for example, in "Santalin—A peerless natural colourant", Cosmetics & Toiletries, Vol. 101, April 1986, page 69.

However, their use as an agent for colouring the skin as defined above has never been described.

The redwood extracts used in the present invention preferably comprise at least one molecule corresponding to the following formula (I):

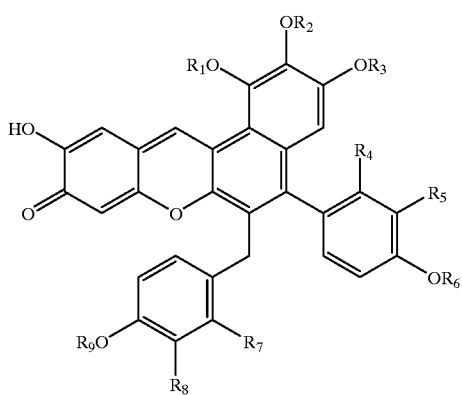

(I)

in which:
$R_1$, $R_2$, $R_3$, $R_6$ and $R_9$, which are identical or different, independently represent a hydrogen atom or a $C_1$–$C_4$ alkyl radical,
$R_4$, $R_5$, $R_7$, and $R_8$, which are identical or different, independently represent a hydrogen atom, a hydroxyl radical or a $C_1$–$C_4$ alkoxy radical.

The compounds used in the present invention are preferably those corresponding to the above formula (I) in which $R_2$ and $R_6$ each represent a hydrogen atom.

A particularly preferred family of compounds suitable for the present invention is that of the compounds corresponding to the above formula (I) in which $R_2$, $R_5$, $R_6$, $R_7$ and $R_9$ each represent a hydrogen atom. A preferred compound of this family is that in which, in addition, $R_1$ and $R_3$ each represent a methyl radical, $R_4$ represents a methoxy radical and $R_8$ represents hydrogen. Another preferred compound of this family is that in which, in addition, $R_1$ and $R_3$ each represent a methyl radical and $R_4$ and $R_8$ each represent a methoxy radical. A third preferred compound of this family is that in which, in addition, $R_1$ and $R_3$ each represent hydrogen and $R_4$ and $R_8$ each represent a hydroxyl radical.

Another particularly preferred family of compounds suitable for the present invention is that of the compounds corresponding to the above formula (I) in which:
$R_2$, $R_4$ and $R_6$ each represent hydrogen,
$R_1$ and $R_3$ each represent a methyl radical,
$R_7$ represents the methoxy radical.

A preferred compound of this second family is that in which, in addition, $R_5$ represents a methoxy radical, $R_8$ represents hydrogen and $R_9$ represents a methyl radical. Another preferred compound of this second family is that in which, in addition, $R_5$ represents a hydroxyl radical, $R_8$ represents hydrogen and $R_9$ represents a methyl radical. A third preferred compound of this second family is that in which, in addition, $R_5$ and $R_8$ each represent a hydroxyl radical and $R_9$ represents hydrogen.

The redwood extract is preferably present in the compositions according to the present invention in proportions sufficient to confer on the skin, after application, a colouring similar to the colouring obtained as a result of natural tanning. It is thus generally present in proportions of between 0.05 and 10% by weight with respect to the total weight of the composition and preferably of between 0.1 and 5% by weight with respect to the total weight of the composition.

The cosmetic and/or dermatological compositions targeted by the present invention can, of course, comprise one or more other agents for colouring the skin, such as, for example, mono- or polycarbonyl derivatives, such as isatin, alloxan, ninhydrin, glyceraldehyde, meso-tartaraldehyde or pyrazoline-4,5-dione derivatives, it being possible for these agents for colouring the skin optionally to be used in combination with direct dyes or indole derivatives.

In a preferred embodiment of the invention, the compositions additionally comprise dihydroxyacetone (DHA).

Another subject-matter of the present invention is thus a cosmetic and/or dermatological composition, characterized in that it comprises, in a cosmetically acceptable vehicle, a redwood extract as defined above and dihydroxyacetone.

This is because dihydroxyacetone and the redwood extracts defined above exhibit excellent chemical compatibility within the compositions comprising them, as well as very good complementarity of the colourings which they confer on the skin, which makes it possible, by combining them in appropriate proportions, to arrive at an artificial colouring of the skin which is remarkably similar to the colouring conferred by natural tanning.

Dihydroxyacetone or DHA is present in the compositions according to the invention in proportions which make it possible for the combination of the two agents for colouring the skin, namely the redwood extract and dihydroxyacetone itself, to confer on the skin, after application, a colouring which is as close as possible to that obtained as the result of natural tanning. DHA is thus generally present in proportions of between 0.5 and 10% by weight with respect to the total weight of the emulsion and preferably of between 1 and 7% by weight with respect to the total weight of the composition.

Dihydroxyacetone can also be applied to the skin in the form of an independent composition, separately from the composition comprising the redwood extract, for example before or after the application of the latter.

In a preferred embodiment of the cosmetic treatment according to the invention, a composition comprising dihydroxyacetone is applied in a first step and then, in a second step, the composition comprising the redwood extract is applied, for the purpose of varying the hue, according to the wish of the user, of the colouring contributed by dihydroxyacetone alone, which is sometimes regarded as being somewhat yellow.

The compositions according to the invention can also comprise one or more hydrophilic or lipophilic sunscreen agents active in the UVA and/or UVB (absorbers) or alternatively coated or uncoated metal oxide pigments.

The compositions in accordance with the present invention can additionally comprise conventional cosmetic adjuvants chosen in particular from fatty substances, organic solvents, ionic or nonionic thickeners, softeners, antioxidants, agents for combating free radicals, opacifiers, stabilizers, emollients, silicones, α-hydroxy acids, antifoaming agents, moisturizing agents, vitamins, fragrances, preservatives, surfactants, fillers, sequestering agents, polymers, propellants, basifying or acidifying agents, dyes or any other ingredient commonly used in the cosmetics and/or dermatological field, in particular for the manufacture of antisun compositions in the form of emulsions.

The fatty substances can be composed of an oil or a wax or their mixtures. The term "oil" is understood to mean a compound which is liquid at room temperature. The term "wax" is understood to mean a compound which is solid or substantially solid at room temperature and which has a melting point generally of greater than 35° C.

Mention may be made, as oils, of mineral oils (liquid petrolatum); vegetable oils (sweet almond oil, macadamia oil, blackcurrant seed oil, jojoba oil); synthetic oils, such as perhydrosqualene, fatty alcohols, acids or esters (such as the benzoate of $C_{12}$–$C_{15}$ alcohols sold under the trade name "Finsolv TN" by the company Finetex, octyl palmitate, isopropyl lanolate or triglycerides, including those of capric/caprylic acids), or oxyethylenated or oxypropylenated fatty esters and ethers; silicone oils (cyclomethicone, polydimethysiloxanes or PDMS); fluorinated oils or polyalkylenes.

Mention may be made, as waxy compounds, of paraffin wax, carnauba wax, beeswax or hydrogenated castor oil.

Mention may be made, among organic solvents, of lower alcohols and polyols.

The thickeners can be chosen in particular from crosslinked polyacrylic acids, guar gums and celluloses which may or may not be modified, such as hydroxypropylated guar gum, methylhydroxyethylcellulose and hydroxypropylmethyl cellulose.

Of course, a person skilled in the art will take care to choose the optional additional compound or compounds mentioned above and/or their amounts so that the advantageous properties intrinsically attached to the use of the compounds of formula (I) above in accordance with the invention are not, or not substantially, detrimentally affected by the envisaged addition or additions.

The compositions according to the invention can be prepared according to techniques well known to a person skilled in the art, in particular those intended for the preparation of emulsions of oil-in-water or water-in-oil type.

This composition can be provided in particular in the form of a simple or complex emulsion (O/W, W/O, O/W/O or W/O/W), such as a cream or a milk, or in the form of a gel or of a cream gel, or in the form of a lotion, powder or solid stick and can optionally be packaged as an aerosol and be provided in the form of a foam or of a spray.

The compositions according to the invention are preferably provided in the form of an oil-in-water emulsion.

When it relates to an emulsion, the aqueous phase of the latter can comprise a nonionic vesicular dispersion prepared according to known processes (Bangham, Standish and Watkins, J. Mol. Biol., 13, 238 (1965), FR 2,315,991 and FR 2,416,008).

Concrete but in no way limiting examples illustrating the invention will now be given.

EXAMPLE 1

This example is targeted at showing, in a first step, the intensity of the colouring obtained with a redwood extract in accordance with the present invention, as well as the speed with which this colouring develops.

In a second step, the improvement, in terms of colouring hue, contributed by a composition according to the invention (Composition A comprising a DHA/redwood extract combination according to the invention) will be shown with respect to a conventional composition comprising only DHA (Composition B).

The Applicant Company has prepared the following Composition A (the amounts are expressed as percentage by weight with respect to the total weight of the composition):

| Composition A: | |
| --- | --- |
| -cetylstearyl glucoside/cetylstearyl alcohol mixture, sold under the trade name "Montanov 68" by Seppic | 7.5% |
| -dimethicone | 0.5% |
| -benzoate of $C_{12}/C_{15}$ alcohols, sold under the trade name "Finsolv TN" by Finetex | 15% |
| -propylene glycol | 10% |
| -dihydroxyacetone | 5% |
| -sandalwood extract, sold in the form of a powder under the trade name "Santal Poudre SL PP" by the company Copiaa | 0.3% |
| -preservatives | q.s. |
| -water | q.s. for 100% |

The Applicant Company has also prepared a Composition B which is identical to A but which does not comprise any sandalwood extract.

Evaluation Protocol:

Compositions A and B were applied at the rate of 1 mg/cm² to an area of 7×7 cm² defined on the backs of four volunteers.

The three series of calorimetric measurements which follow were carried out using a Minolta CM-1000 colorimeter:

–1°) before application of the composition ($T_0$)

–2°) 30 minutes after application ($T_{30\ min}$),

–3°) 5 hours after application and after washing ($T_{5H}$).

The results are expressed in the (L*, a*, b*) system, in which L* represents the brightness, a* represents the red-green axis (–a*=green, +a*=red) and b* represents the yellow-blue axis (–b*=blue, +b*=yellow). Thus, a* and b* express the hue of the skin.

The matters of interest in evaluating the intensity of the colouring are:

ΔL*, which reflects the darkening in the colour: the more negative ΔL*, the more the colour has darkened, the Δa*/Δb* ratio, which reflects the red-yellow balance and therefore the hue.

The results obtained are collated in the following Table (I):

TABLE (I)

|  |  | Composition A (invention) | Composition B (comparative) |
|---|---|---|---|
| $\Delta a^*$ (mean) | at $T_{30\ min}$ | 2.59 | — |
|  | at $T_{5H}$ | 1.06 | 0.91 |
| $\Delta b^*$ (mean) | at $T_{30\ min}$ | 2.49 | — |
|  | at $T_{5H}$ | 1.36 | 1.45 |
| $\Delta L^*$ (mean) | at $T_{30\ min}$ | −1.74 | 0.13 |
|  | at $T_{5H}$ | −0.86 | −0.94 |
| $\Delta a^*/\Delta b^*$ (mean) | at $T_{30\ min}$ | 1.05 | — |
|  | at $T_{5H}$ | 0.81 | 0.63 |

It is thus found that, 30 minutes after application, Composition B, which comprises only DHA, has conferred virtually no colouring on the skin, since the DHA has not yet had the time to act ($\Delta L^*=0.13$). On the other hand, the composition according to the invention has already conferred a significant colouring ($\Delta L^*=-1.74$) on the skin while retaining a good red-yellow balance ($\Delta a^*/\Delta b^*=1.05$). Thus, the sandalwood extract in accordance with the invention confers on the skin, entirely by itself alone, an intense colouring similar to natural tanning.

Furthermore, it is found that, 5 hours after application of the compositions and after washing, the two compositions A and B have conferred on the skin a darkening of similar intensity ($\Delta L^*=-0.86$ and $\Delta L^*=-0.94$) due to the action of DHA but that Composition A according to the invention confers on the skin a colouring which is much less yellow than DHA and much closer to the red-yellow balance ($\Delta a^*/\Delta b^*=0.81$ against $\Delta a^*/\Delta b^*=0.63$ for Composition B).

Thus, the composition according to the invention confers on the skin a colouring which is particularly close to natural tanning and does so very quickly.

EXAMPLE 2

The Applicant Company has prepared the two following compositions C (according to the invention) and D (composition comprising only DHA) (the amounts are expressed as percentage by weight with respect to the total weight of the composition):

| Composition C: | |
|---|---|
| -cetylstearyl glucoside/cetylstearyl alcohol mixture, sold under the trade name "Montanov 68" by Seppic | 7.5% |
| -dimethicone | 0.5% |
| -benzoate of $C_{12}/C_{15}$ alcohols, sold under the trade name "Finsolv TN" by Finetex | 15% |
| -propylene glycol | 10% |
| -dihydroxyacetone | 5% |
| -alcoholic extract of Pterocarpus soyauxii in the form of a powder* | 0.3% |

| Composition C: | |
|---|---|
| -preservatives | q.s. |
| -water | q.s. 100% |

*The alcoholic extract of Pterocarpus soyauxii in the form of a powder was obtained according to the following extraction method: reddish wood from Pterocarpus soyauxii is split up into small twigs which are passed into a Thermomix 3300 (Vorweck) mixer. This first coarse milled material is subsequently subjected to a Retsch mill equipped with a 0.5 mm screen. 50 g of powder are placed in a column surmounted by a separating funnel filled with alcohol (60° EtOH, 500 ml). Percolation is carried out at a flow rate of 30 to 50 ml/hour. The eluent collected is evaporated and then dried under vacuum over $P_2O_5$.

Composition D is identical to Composition C but does not comprise any Pterocarpus soyauxii [lacuna].

Evaluation Protocol:

Compositions C and D were applied twice, at an interval of 24 hours, at the rate of 1 mg/cm² to an area of 7×7 cm² defined on the backs of four volunteers.

The calorimetric measurements were carried out using a Minolta CM-1000 calorimeter before application of the composition ($T_0$) and then 5 hours after the second application ($T_{24+5}$).

As in Example 1, the results are expressed in the L*, a*, b* system.

$$\Delta a^* = a^*_{T_{24+5}} - a^*_{T_0}$$

$$\Delta b^* = b^*_{T_{24+5}} - b^*_{T_0}$$

The results are collated in Table (II) below:

TABLE (II)

|  | Composition C (invention) | Composition D (comparative) |
|---|---|---|
| $\Delta a^*$ (mean) | 4.61 | 2.82 |
| $\Delta b^*$ (mean) | 4.77 | 4.50 |
| $\Delta a^*/\Delta b^*$ (mean) | 0.94 | 0.64 |

Just as in the preceding example, the value of $\Delta a^*/\Delta b^*$ is higher for the composition of the invention: thus it is that the colouring conferred by this composition on the skin has a redder hue than that conferred by the composition comprising only DHA, which is too yellow. Thus, the colouring conferred by the composition according to the invention on the skin is much closer to the red-yellow balance and therefore closer to the colouring contributed by natural tanning.

A composition such as Composition C makes it possible to quickly achieve a first colouring and then, after the development of the DHA, to obtain a lasting colouring very similar to that conferred by natural tanning.

What is claimed is:

1. Cosmetic and/or dermatological composition intended to confer to the skin an artificial coloring, wherein said composition comprises in a cosmetically acceptable vehicle, an effective amount of at least one redwood extract as an agent for coloring the skin and dihydroxyacetone (DHA).

2. Composition according to claim 1, wherein the redwood comprises "insoluble" redwoods.

3. Composition according to claim 2, wherein the redwood is of the genus "Pterocarpus" or of the genus "Baphia".

4. Composition according to claim 3, wherein the redwood is of the genus "Pterocarpus".

5. Composition according to claim 4, wherein the extract is obtained by basic aqueous extraction of *Pterocarpus santalinus*.

6. Composition according to claim 4, wherein the extract is obtained by aqueous/alcoholic extraction of *Pterocarpus soyauxii*.

7. Composition according to claim 1, wherein the extract is present in the final composition at a content ranging from 0.05 to 10% by weight with respect to the total weight of the composition.

8. Composition according to claim 1, wherein the extract comprises at least one compound of following formula (I):

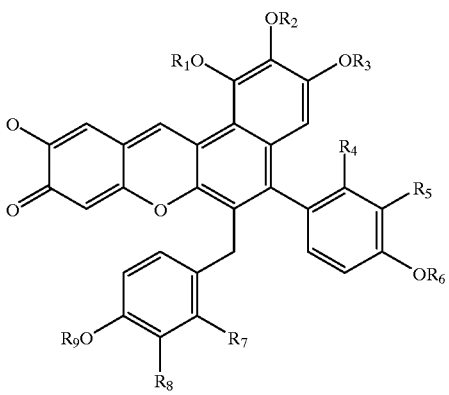

in which:

$R_1$, $R_2$, $R_3$, $R_6$ and $R_9$, which are identical or different, represent a hydrogen atom or a C1–C4 alkyl radical, $R_4$, $R_5$, $R_7$ and $R_8$, which are identical or different, represent a hydrogen atom, a hydroxyl radical or a $C_1$–$C_4$ alkoxy radical.

9. Cosmetic and/or dermatological composition, comprising, in a cosmetically acceptable vehicle, an effective amount of at least one compound of following formula (I):

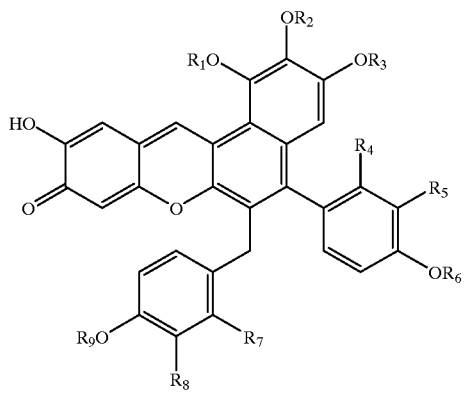

in which:

$R_1$, $R_2$, $R_3$, $R_6$ and $R_9$, which are identical or different, represent a hydrogen atom or a $C_1$–$C_4$ alkyl radical, $R_4$, $R_5$, $R_7$ and $R_8$, which are identical or different, represent a hydrogen atom, a hydroxyl radical or a $C_1$–$C_4$ alkoxy radical, as an agent for coloring the skin and dihydroxyacetone (DHA).

10. Composition according to claim 8, wherein the $R_2$ and $R_6$ radicals each represent a hydrogen atom.

11. Composition according to claim 8, wherein the compound of formula (I) is a santalin.

12. Composition according to claim 8, wherein the compound of formula (I) is a santarubin.

13. Composition according to claim 8, wherein it additionally comprises another agent for coloring the skin.

14. Composition according to claim 13, wherein said agent is a mono- or polycarbonyl derivative.

15. Composition according to claim 14, wherein said mono- or polycarbonyl derivatives are selected from the group consisting of isatin, alloxan, ninhydrin, glyceraldehyde, meso-tartaraldehyde or pyrazoline-4,5-dione derivatives.

16. Composition according to claim 8, wherein said dihydroxyacetone is present in the composition at a content ranging from 0.5 to 10% by weight with respect to the total weight of the composition.

17. Process for the cosmetic treatment of the skin intended to confer on said skin an artificial coloring, comprising the following two stages:
i) applying a composition comprising dihydroxyacetone to the skin,
ii) when the desired coloring contributed by the dihydroxyacetone has developed on the skin, applying the composition according to claim 1 to the skin in order to vary the hue of the coloring.

* * * * *